United States Patent [19]

Hall, II

[11] Patent Number: 5,167,160

[45] Date of Patent: Dec. 1, 1992

[54] POSITIONING DEVICE FOR PRESENTING SAMPLES FOR ELECTROMAGNETIC ANALYSIS

[75] Inventor: Lacy L. Hall, II, Elkhart, Ill.

[73] Assignee: Agmed, Inc., Springfield, Ill.

[21] Appl. No.: 710,589

[22] Filed: Jun. 5, 1991

[51] Int. Cl.$^5$ .............................................. G01N 1/28
[52] U.S. Cl. ................................ 73/864.91; 119/17; 138/119; 138/122; 356/244
[58] Field of Search ................. 73/864.91, 863; 324/321; 356/36, 244; 138/118.1, 119, 122; 285/417, 383; 378/208; 119/17; 43/60, 85

[56] References Cited

U.S. PATENT DOCUMENTS

| | | | |
|---|---|---|---|
| 382,468 | 5/1888 | Haley | 285/383 X |
| 1,074,916 | 10/1913 | Wiesen | 43/65 |
| 2,441,055 | 5/1948 | Babigion | 285/383 |
| 3,058,493 | 10/1962 | Muller | 138/122 |
| 3,275,038 | 9/1966 | Robert et al. | 138/122 |
| 3,833,075 | 9/1974 | Bachman et al. | 175/20 |
| 3,884,509 | 5/1975 | Marsh, Jr. | 285/342 X |
| 4,224,950 | 9/1980 | Bore et al. | 356/36 X |
| 4,384,626 | 5/1983 | Derouin | 175/57 X |
| 4,495,795 | 1/1985 | Gupta | 73/38 |
| 4,496,907 | 1/1985 | Funk et al. | 324/445 |
| 4,727,330 | 1/1985 | Funk et al. | 324/445 |
| 4,905,267 | 2/1990 | Miller et al. | 378/208 |

FOREIGN PATENT DOCUMENTS

| | | | |
|---|---|---|---|
| 247679 | 6/1966 | Austria | 285/417 |
| 104389 | 5/1898 | Fed. Rep. of Germany | 138/122 |
| 1173257 | 2/1959 | France | 138/122 |
| 546112 | 7/1956 | Italy | 138/122 |
| 293595 | 1/1971 | U.S.S.R. | 378/208 |
| 2144238 | 2/1985 | United Kingdom | 73/864.91 |

Primary Examiner—Tom Noland
Attorney, Agent, or Firm—Trexler, Bushnell, Giangiorgi & Blackstone, Ltd.

[57] ABSTRACT

Positioning apparatus for presenting a sample for electromagnetic analysis comprises a flexible, resilient, generally cylindrical, open-ended inner sleeve member having a lengthwise through slit, such that the effective diameter thereof is adjustable over a predetermined range in response to radially inward compression thereof. An elongate constricting assembly surroundingly engages and selectively applies radially inward compression to the inner sleeve member. The constricting assembly comprises a pair of generally rigid, cylindrical axially spaced gripping members and a plurality of resilient, helical members coupled intermediate the gripping members. The helical members are responsive to relative rotation of the gripping members in a first direction for applying radially inward compression to the inner sleeve member, and responsive to relative rotation of the gripping members in an opposite direction for releasing radially inward compression on the inner sleeve member.

12 Claims, 2 Drawing Sheets

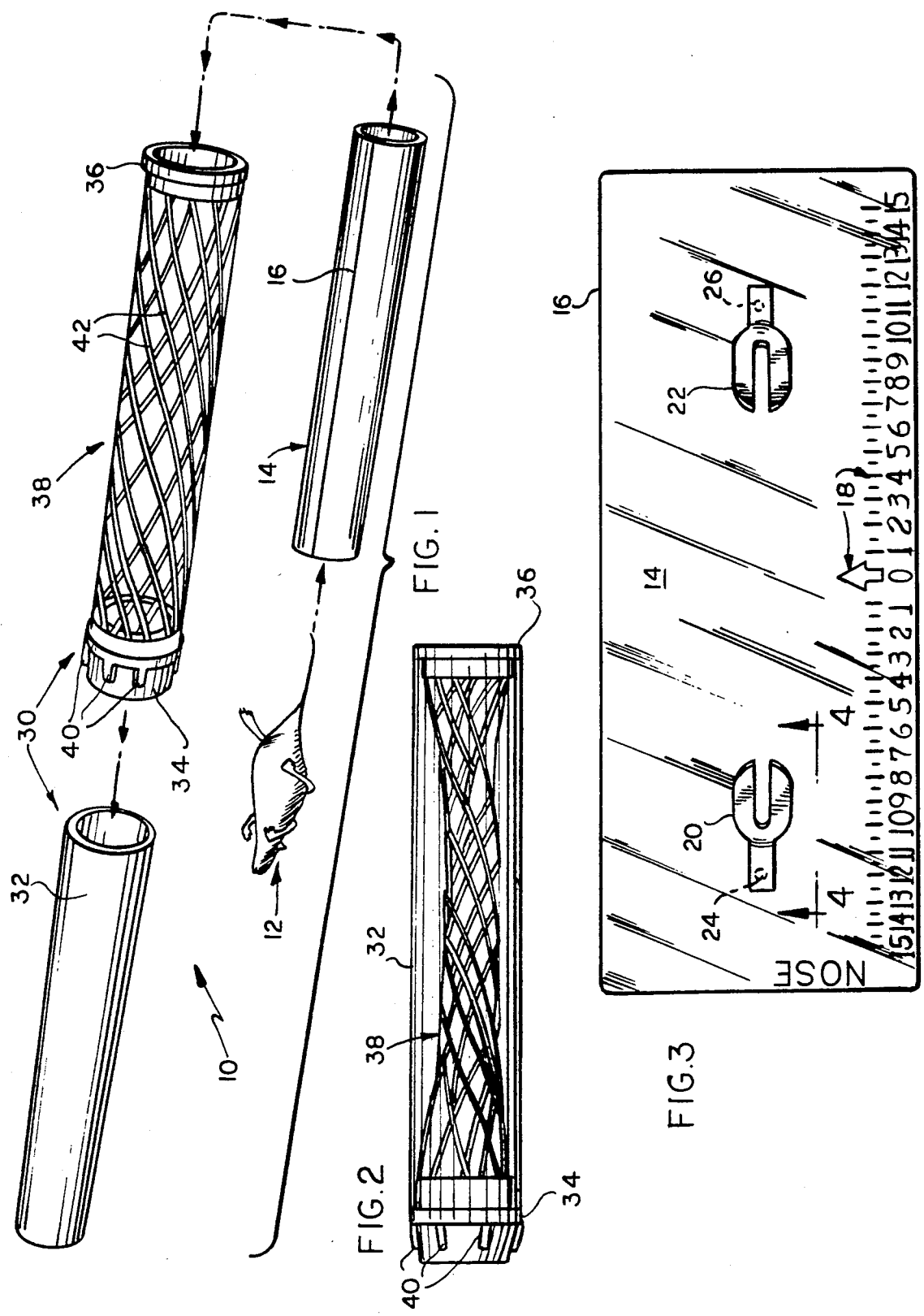

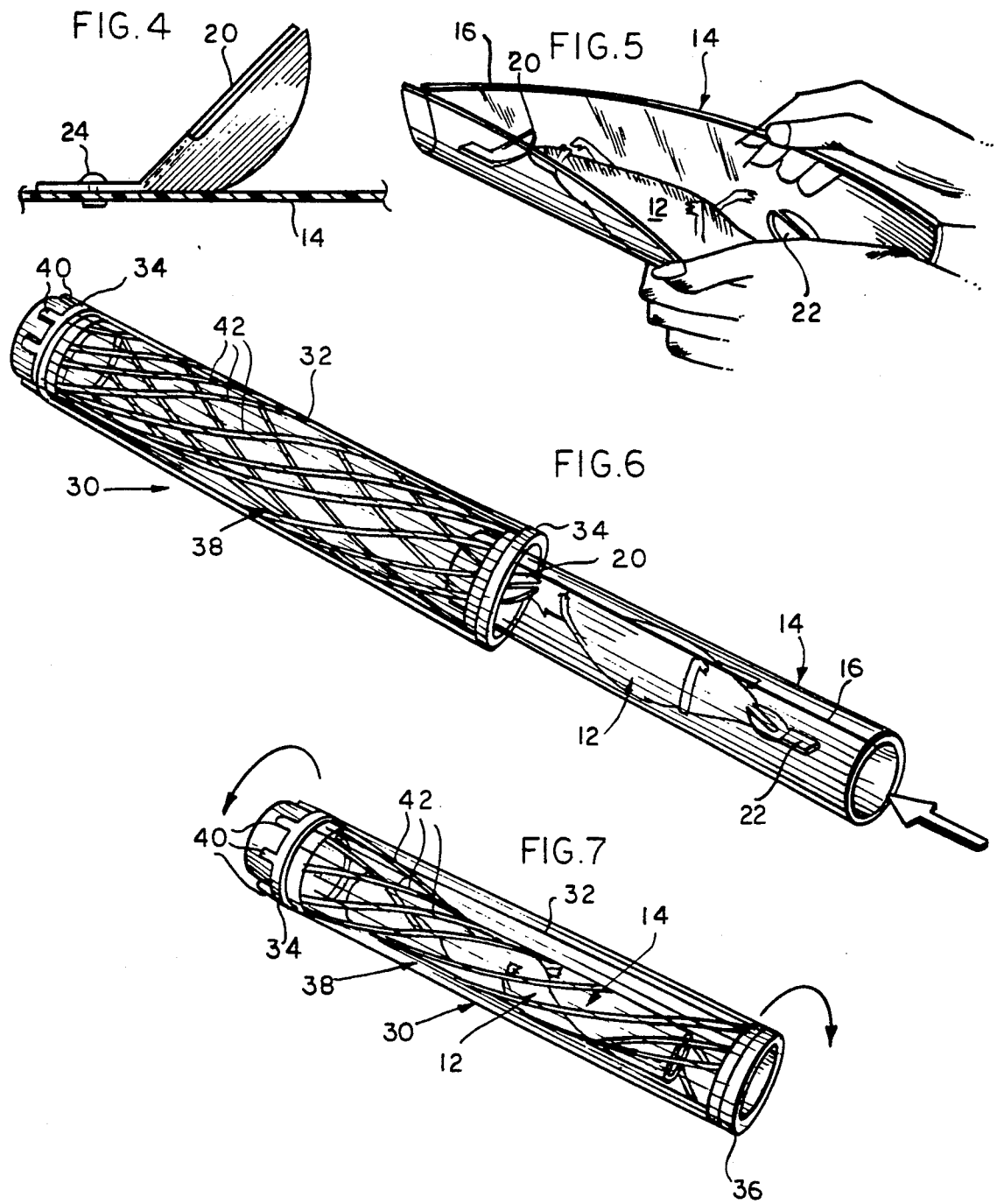

POSITIONING DEVICE FOR PRESENTING SAMPLES FOR ELECTROMAGNETIC ANALYSIS

BACKGROUND OF THE INVENTION

This application is directed generally to the problem of properly positioning a sample for testing within an analysis instrument of the type which presents a generally elongate cylindrical test chamber, and more particularly to a positioning apparatus for presenting a sample for analysis in such a device.

While the apparatus of the invention may find other applications, the invention will be particularly described herein with reference to the problem of positioning an object or sample to be presented to an electromagnetic analysis apparatus. One such apparatus is generally shown and described in U.S. Pat. No. 4,496,907 which is commonly owned herewith. In this prior U.S. patent, a test apparatus is shown which utilizes an electromagnetic field in order to determine conductivity-related properties of a sample of material which is introduced into the apparatus. This test apparatus may be utilized for testing relatively uniform bulk materials, such as agricultural grains, samples of prepared ground meats and the like in agricultural commodities-related applications.

Similar apparatus for measuring certain properties of human or animal subjects is shown and described in U.S. Pat. No. 4,727,330, which is also commonly owned herewith. This apparatus also utilizes an electromagnetic field to determine conductivity-related properties of the subject.

When using test apparatus similar to those shown in the above-referenced U.S. patents with small animals in laboratory settings, some difficulties arise. For example, it is generally desirable to present a sample or subject of generally uniform shape and orientation, and to hold the subject substantially centered with respect to the electromagnetic field in the measurement chamber of the measurement device or apparatus. This is desirable primarily to assure uniformity of shape and orientation from one sample or subject to the next, and hence to assure relatively uniform measurement results from one sample or subject to the next. Generally speaking, the laboratory animal presented to the test instrument is living, however, the animal may or may not be anesthetized. Such laboratory animals are generally irregular and non-uniform in shape, and may therefore be difficult to properly present for analysis.

OBJECTS AND SUMMARY OF THE INVENTION

Accordingly, it is a general object of the invention to provide a positioning device which presents a subject of substantially uniform shape and orientation substantially centered in the chamber of a test instrument.

A related object is to provide a positioning device in accordance with the foregoing object which applies a generally uniform radial pressure to the subject, conforming it to a generally cylindrical shape and simultaneously holding it centered substantially both radially and axially relatively to the center of the electromagnetic field of the test instrument.

A related object is to provide a positioning device in accordance with the foregoing object, wherein the device is constructed entirely of nonconductive and preferably of plastics materials which will have substantially no effect on operation of a conductivity-sensing electromagnetic measurement system.

Briefly, and in accordance with the foregoing objects, the present invention provides a positioning apparatus for presenting a sample for analysis comprises flexible, resilient, open-ended generally cylindrical inner sleeve means for surroundingly engaging said sample, said sleeve means being resiliently deformable such that the inner diameter thereof is adjustable over a predetermined range in response to radial resultant compressive forces applied thereto, and elongate constricting means for surroundingly engaging and selectively applying said resultant radial forces to said inner sleeve means, said constricting means comprising a pair of generally cylindrical axially spaced gripping means for relative manual rotation and resiliently deformable helical means coupled between said gripping means and responsive to relative rotation of said gripping means in a first direction for applying said resultant radial force in a direction for inwardly compressing said inner sleeve means and responsive to relative rotation of said gripping means in an opposite direction for releasing said resultant radially inward compressive force on said inner sleeve means.

BRIEF DESCRIPTION OF THE DRAWINGS

The features of the present invention which are believed to be novel are set forth with particularity in the appended claims. The organization and manner of the operation of the invention, together with further objects and advantages thereof may best be understood by reference to the following description, taken in connection with the accompanying drawings in which like reference numerals identify like elements, and in which:

FIG. 1 is an exploded perspective view illustrating components of a positioning device in accordance with the invention in connection with a subject to be positioned within a test instrument;

FIG. 2 is an assembled view of the positioning device of FIG. 1, illustrating operation of the same for radially inwardly compressing the test subject to a generally cylindrical form substantially radially and axially centered therein;

FIG. 3 is an enlarged plan view of a flexible resilient inner sleeve portion of the device of FIG. 1;

FIG. 4 is an enlarged partial sectional view taken generally along the line 4—4 of FIG. 3;

FIG. 5 is a perspective view illustrating placement of a subject within the inner sleeve member of FIG. 3;

FIG. 6 is a perspective view illustrating placement of the inner sleeve member with subject, into a further constricting assembly portion of the device of the invention; and FIG. 7 is a perspective view illustrating manipulation of the constricting assembly for accomplishing the desired radial compression and substantial radial and axial centering of the test subject.

DETAILED DESCRIPTION OF THE ILLUSTRATED EMBODIMENT

Referring now to the drawings and initially to FIG. 1, a positioning apparatus for presenting a sample for analysis is shown in exploded perspective view and indicated generally by the reference numeral 10. One typical such sample or subject for analysis is a laboratory animal, indicated generally by reference numeral 12.

In accordance with the invention, the subject 12 is placed in a flexible, resilient, open-ended generally cylindrical inner sleeve 14. Preferably, the inner sleeve has an elongated axial through slit 16 to permit the same to be readily partially opened for placing the subject 12 therewithin. However, the sleeve maintains its generally cylindrical shape or set so as to readily surroundingly engage the subject 12. The slit 16 further permits resilient radially inward deformation of the sleeve 14, such that the inner diameter thereof is adjustable over a given range in response to a resultant radial compressive force being applied thereto. Hence, the generally cylindrical inner sleeve 14 may be radially inwardly compressed to apply a generally uniform radial pressure to the subject, conforming it generally to a cylindrical shape.

Preferably, the inner sleeve 14 is constructed of a clear transparent butyrate tubing, the outer diameter thereof being selected in accordance with the relative size of the subject 12. We prefer to provide the inner sleeve 14, in a range of sizes having outer diameters in one-half inch increments from substantially on the order of 1.5 inches to 3.0 inches. In the illustrated embodiment, the axial length of the sleeve 14 is 15.0 inches for a 3.0 inch outer diameter. However, we prefer to provide a 13.0 inch axial length of sleeve 14 for the smaller outer diameters as mentioned above. Preferably, the gage of the butyrate material forming sleeve 14 provides a wall thickness thereof of substantially on the order of 0.030 inches. Preferably, the four corners defined by the axial slit 16 are slightly rounded, as best viewed in FIG. 3.

Referring briefly to FIG. 3, in accordance with the preferred form of the invention illustrated therein, the inner sleeve 14 is further provided with graduated axial indicia 18 for facilitating the positioning of the sample or subject 12 in a substantially axially centered position therein. Moreover, the inner sleeve 14 also preferably includes respective resiliently deformable flaps 20, 22 which are attached thereto at axially spaced locations to at least partially close the open ends thereof when the same is engaged about the subject 12. The flaps 20 and 22 may be attached by adhesive or mechanical means to the inner sleeve 14. Small brads or rivets 24, 26 are indicated in FIGS. 3 and 4. FIG. 5 illustrates in somewhat greater detail the placement of the subject 12 within inner sleeve 14 preparatory to presenting the same for analysis.

In order to provide radially inward compressive force to the sleeve 14 and also to hold the same and the subject 12 in substantially radially and axially centered position relative to a generally cylindrical test chamber, the invention further provides an elongated constricting means or assembly indicated generally by reference numeral 30. In the illustrated embodiment, the constricting assembly 30 includes a rigid, open-ended cylindrical outer sleeve or tube member 32. The outer sleeve or tube 32 is of a diameter and axial length appropriate for mounting a pair of generally cylindrical gripping members 34, 36 for relative rotation and in an axially spaced apart condition. These gripping members 34, 36 mount therebetween resiliently deformable helical means 38.

With the gripping means 34 and 36 held in a fixed, axially spaced condition by outer cylinder or tube 32, relative rotation of the gripping members 34, 36 will cause inward and outward radial movement of the helical means or assembly 38 for a corresponding application of resultant radial force or release thereof relative to the inner sleeve 14 and subject 12 received therein.

This sort of radial inward compression as shown in FIGS. 2 and 7 for example. That is, relative rotation of the gripping means 34 and 36 in first direction or sense as indicated in FIG. 7 causes relative inward compression of the helical means 38, while opposite relative rotation thereof will release this compression and permit the helical means to return to its relaxed or uncompressed state as illustrated for example in FIGS. 1 and 6.

Preferably, the gripping member or means 34 is of enlarged form and includes a plurality of circumferentially spaced raised ridges 40 to facilitate manual gripping and rotation thereof. During such gripping and rotation, the opposite gripping member 36 is held stationary relative to the tube 32. End 36 may therefore be either rotatable relative to tube 32 and manually held in place during gripping and rotation of member 34, or alternatively, end 36 may be affixed to tube 32 in a non-rotatable condition.

Preferably, the helical means or member 38 comprises a plurality of elongated, spaced apart generally helically arranged strips 42 of flexible material. Each of these strips 42 has its opposite ends respectively joined to respective gripping or end members 34, 36. In the preferred and illustrated embodiment these helical strips are eight in number and extend through a helix of substantially 225° when the assembly is at its maximum or relaxed diameter as shown in FIGS. 1 and 6 for example. Preferably, the gripping member 34 is rotatable through substantially an additional 180° from the position shown in FIGS. 1 and 7 for adding substantially 180° to the helix defined by the respective strips 42 and thereby correspondingly reducing the diameter of at least a central portion 44 of the helical means 38 as shown for example in FIGS. 2 and 7.

Preferably, the outer sleeve or cylinder 32 is also constructed of clear butyrate tubing, having an outer diameter of on the order of 3.0 inches, a wall thickness of substantially 0.050 inches and an axial length of substantially 15.0 inches. The strips 42 which form the eight-element helix 38 are each substantially 0.20 inches wide by 0.06 inches thickness and 16 inches in length, and these members are molded into the tube or gripping member 34, 36. Preferably, the gripping members ends 34, 36 are formed of cast epoxy material and the strips 42 are nylon.

In use, as illustrated in FIGS. 5 through 7, the outer sleeve 32 holds the ends 34 and 36 at a fixed spacing and at the proper orientation. The subject 12 is placed within the inner sleeve 14 by prying the sleeve apart at slit 16 to form a generally U-shaped trough to receive the subject. The inner sleeve is then allowed to resiliently return to its generally cylindrical shape about the subject. The helix 38 is rotated, by grasping and rotating a gripping member 34, to its maximum diameter as shown in FIG. 6. Thereupon, the inner sleeve 14 containing the subject 12 may be inserted through one open end of the assembly 30 as shown in FIG. 6. The ends 34 and 36 are then relatively rotated to compress the central part of helical means 38 and thus compress the inner sleeve 14 and subject 12. This conforms the subject to a nearly cylindrical shape (without any injury) and also serves to center the subject both axially and radially relative to assembly 30. Since assembly 30 fits substantially concentrically within the test instrument, this has the effect of substantially centering the subject within the instrument itself and within the electromagnetic field utilized within the test chamber of the instrument.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A positioning apparatus for presenting a sample for analysis comprising: flexible, resilient, open-ended generally cylindrical inner sleeve means for surroundingly engaging said sample, said sleeve means being resiliently deformable such that the inner diameter thereof is adjustable over a predetermined range in response to radial resultant compressive forces applied thereto, and elongate constricting means for surroundingly engaging and selectively applying said resultant radial forces to said inner sleeve means, said constricting means comprising a pair of generally cylindrical axially spaced gripping means for relative manual rotation and resiliently deformable helical means coupled between said gripping means and responsive to relative rotation of said gripping means in a first direction for applying said resultant radial force in a direction for inwardly compressing said inner sleeve means and responsive to relative rotation of said gripping means in an opposite direction for releasing said resultant radially inward compressive force on said inner sleeve means.

2. Apparatus according to claim 1 wherein inner sleeve means comprises an open-ended cylindrical member having a lengthwise through slit.

3. Apparatus according to claim 1 wherein said helical means comprises a plurality of elongate spaced apart generally helically arranged strips of flexible material, each strip having opposite ends thereof respectively joined to the respective gripping members.

4. Apparatus according to claim 3 wherein said strips are eight in number.

5. Apparatus according to claim 3 wherein said gripping members are relatively rotatable through substantially 180°.

6. Apparatus according to claim 3 wherein said helical means is radially inwardly resiliently deformable in response to relative rotation of said gripping means, from a maximum diameter substantially equal to the diameter of said gripping means.

7. Apparatus according to claim 6 wherein each of said strips extends through a helix of substantially 225° when said helical means is at its maximum diameter and wherein said gripping means are rotatable for adding substantially 180° to said helix of said strips and correspondingly reducing the diameter of a central portion of said helical means.

8. Apparatus according to claim 1 wherein a central portion of said helical means is resiliently radially inwardly deformable in response to relative rotation of said gripping means from a maximum diameter substantially equal to the diameter of said gripping means.

9. Apparatus according to claim 1 wherein said constricting means further includes a relatively rigid outer cylindrical sleeve member for surrounding said helical means and respectively engaging said gripping means for holding the same axially spaced apart by a predetermined fixed distance, while permitting said relative rotation thereof.

10. Apparatus according to claim 1 wherein said inner sleeve means further includes graduated axial indicia means for facilitating positioning of a sample in a substantially axially centered position therein.

11. Apparatus according to claim 1 wherein said inner sleeve means further includes resiliently deformable flap means for at least partially closing open ends thereof when the same is engaged about a sample.

12. Positioning apparatus for presenting a sample for electromagnetic analysis comprising: a flexible, resilient, generally cylindrical, open-ended inner sleeve member having a lengthwise through slit, such that the effective diameter thereof is adjustable over a predetermined range in response to radially inward compression thereof; and an elongate constricting assembly for surroundingly engaging and selectively applying said radially inward compression to said inner sleeve member; said constricting assembly comprising a pair of generally rigid, cylindrical axially spaced gripping members and a plurality of resilient, helical members coupled intermediate said gripping members, said helical members being responsive to relative rotation of said gripping members in a first direction for applying said radially inward compression to said inner sleeve member, and responsive to relative rotation of said gripping members in an opposite direction for releasing said radially inward compression on said inner sleeve member.

* * * * *